(12) United States Patent
Davis et al.

(10) Patent No.: US 7,280,871 B2
(45) Date of Patent: Oct. 9, 2007

(54) MUSCLE STIMULATION SYSTEMS (75) Inventors: Glen Macartney Davis, Petersham (AU); Peter James Sinclair, Marrickville (AU); Che Fornusek, Randwick (AU)

(73) Assignee: The University of Syndey, Sydney, New South Wales (AU)

( * ) Notice: Subject to any disclaimer, the term of this patent is extended or adjusted under 35 U.S.C. 154(b) by 186 days.

(21) Appl. No.: 10/492,805

(22) PCT Filed: Oct. 21, 2002

(86) PCT No.: PCT/AU02/01430

§ 371 (c)(1),
(2), (4) Date: Sep. 3, 2004

(87) PCT Pub. No.: WO03/032887

PCT Pub. Date: Apr. 24, 2003

(65) Prior Publication Data

US 2005/0015118 A1    Jan. 20, 2005

(30) Foreign Application Priority Data

Oct. 19, 2001  (AU) .................................. PR 8376
Dec. 11, 2001  (AU) .................................. PR 9427

(51) Int. Cl.
*A61N 1/00*      (2006.01)

(52) U.S. Cl. ........................ 607/48; 607/49; 482/8
(58) Field of Classification Search .......... 607/48, 607/49; 482/8
See application file for complete search history.

(56) References Cited

U.S. PATENT DOCUMENTS

| 4,492,233 | A  | * | 1/1985 | Petrofsky et al. ............. 607/48 |
| 4,499,900 | A  | * | 2/1985 | Petrofsky et al. ............. 607/48 |
| 4,724,842 | A  | * | 2/1988 | Charters ....................... 607/48 |
| 4,947,836 | A  | * | 8/1990 | Laenger et al. ............... 607/48 |
| 6,267,709 | B1 | * | 7/2001 | Jacques et al. ................ 482/8 |
| 2004/0023759 | A1 | * | 2/2004 | Duncan et al. ............... 482/57 |

* cited by examiner

*Primary Examiner*—Carl Layno
*Assistant Examiner*—Brian T. Gedeon
(74) *Attorney, Agent, or Firm*—Kelly Lowry & Kelley, LLP (57) ABSTRACT

A control system for controlled exercise controls a functional electrical stimulation (FES) system which applies electrical signals to muscle groups of a user such as a user having a disability; the user exercises on a motor driven exercise machine such that substantially isokinetic exercise during a movement is obtained as the user's body part moves with a motor driven displaceable element of the machine. This element provides resistance to applied displacement load from the user's stimulated muscles. A feedback control system receives signals indicative of the user's performance and a control arrangement controls electrical stimulation to the user's muscles to achieve a desired exercise regime.

24 Claims, 4 Drawing Sheets

MUSCLE STIMULATION SYSTEMS

FIELD OF THE INVENTION

The present invention relates to a control system and applications of such control systems to the field of electrical stimulation of muscles for the purpose of an exercise program. By way of example, the invention will be illustrated with reference to controlling a functional electrical stimulation (FES) system to induce leg muscle contractions that permit a user with a physical disability to benefit from such exercise. One important example is to apply the invention to use of a machine that simulates cycling motion, but the principles of the invention may be applied to other machines.

BACKGROUND TO THE INVENTION

FES systems have been published in the prior art literature such as U.S. Pat. No. 4,499,900 (Petrofsky et al) and U.S. Pat. No. 4,838,272 (Lieber). One system that has been commercially developed and relates to the Petrofsky teachings is that marketed by Electrologic of America Inc, with a system known as StimMaster Orion, which uses FES as a form of therapeutic treatment. Controlled electrical stimulation currents are passed through electrodes to initiate muscle contractions, for example in the lower extremities of a paralysed patient, thereby causing pedalling of an exercise cycle. The Petrofsky system uses position sensors to measure the position of pedals and these signals are used to control the generation of stimulation signals to the user's electrodes. The aim of these systems is to elicit a constant pre-set velocity of pedalling as a therapeutic treatment for disabled persons, such as paraplegics. In the event that the velocity of cycling does not achieve the desired pedal cadence (preset to 50 rev·min$^{-1}$), then the apparatus will increase or decrease the stimulation amplitude delivered to muscles to change the speed back to the desired pedal cadence.

Such prior art systems rely solely upon applied stimulation to the limbs to initiate and control the exercise being undertaken. Therefore, should the individual wish to exercise at a greater level or intensity, the amount of stimulation applied to the limbs must be increased to this level to achieve such intensity. The likelihood of over-stimulation of the muscles is therefore greatly increased and the potential of such systems to cause permanent damage to the recipient is high. For this reason such exercise systems have not been widely accepted as therapeutic devices.

The Lieber U.S. Pat. No. 4,838,272 discloses adaptive closed loop electrical stimulation of muscles by a technique including applying electrical stimulation signals to selected muscles at a predetermined frequency, pulse width and amplitude. The work output achieved by the muscles in response to stimulation signals is determined over a period of time, and can be compared with target values. The amount of electrical energy delivered to the muscles by stimulation signals is varied in response to the results in order to maximise the work output of the muscles during a treatment period, this being accomplished by adjusting the frequency or pulse width during stimulation treatment in response to the work output measured.

Such a system also has the problem that should the individual wish to perform high intensity exercise then they are solely reliant on increasing the amount of electrical energy delivered to the muscles. Such an increase can therefore cause over stimulation of the muscles and risks causing permanent damage in much the same manner as the systems described above.

Another known class of exercise machine for therapy purposes, particularly for paraplegics having minimal or no muscle function, is one in which the user is passive and the machine such as a cycle exerciser is motor driven to drive at a selected speed whereby the user's limbs follow and are thus exercised. Such systems, whilst reducing the risk of over stimulation of the muscles and permanent damage associated therewith, are limited in the amount of benefit they can provide with regard to muscle strength and/or cardiorespiratory exercise training.

Further publications related to the present field are U.S. Pat. No. 4,724,842 (Charters), EP 103490 (Wright State University), U.S. Pat. No. 6,267,709 (Jacques et al), U.S. Pat. No. 4,865,315 (Paterson et al), U.S. Pat. No. 4,586,510 A (Glaser et al) and U.S. Pat. No. 4,653,479 A (Maurer).

SUMMARY OF THE INVENTION

The present inventors consider that new and useful alternatives to prior art proposals would be desirable and, as described below, have conceived a new combination of features that implement new concepts of controlled exercise for patients having a physical disability.

The present invention, in one aspect, basically consists in a system including:
(a) a motor-driven exercise machine for a user;
(b) a functional electrical stimulation (FES) system for selected muscle groups of a user corresponding to those to be used on the exercise machine;
(c) a feedback control system that receives signals indicative of the user's performance during exercise; and
(d) the system being characterised by means for controlling the FES system to the user's muscles to maintain a desired exercise regime.

More specifically an important embodiment of the invention consists in a system including:
(a) an exercise machine having displaceable means for moving with a body part of a user;
(b) a motor arranged to drive the displaceable means at a selected but normally substantially constant speed and providing a resistance for resisting displacement load from the user's body part applied to the displacement means;
(c) a functional electrical stimulation (FES) system for selected muscle groups of the user corresponding to the body party to be exercised on the exercise machine;
(d) a feedback control system that receives signals indicative of the user's performance during exercise; and
(e) means for controlling the FES system, including means for controlling the electrical stimulation applied to the selected muscle groups in response to the user's performance detected by the feedback control system.

Embodiment of the invention include FES deployed by either skin-surface or surgically implanted systems.

It is to be understood the invention may be implemented to various embodiments including cycling type exercise, as well as other exercises which may be of the nature of a push-pull motion or indeed any motion where a relevant muscle or muscle group is stimulated so that, apart from initial acceleration and deceleration the muscle group is operating in a substantially constant work mode ie constant velocity or constant speed mode. In this specification exercise of this character will be for convenience referred to as isokinetic exercise. This type of exercise includes the case where there may be passive, assisted or even stimulated return to an initial position for a further exercise motion.

Embodiments of the present invention aims at overcoming the problems associated with prior art systems by providing a control system for a FES system that is capable of providing safe and effective stimulation of muscles which may be described as reliant on a combination of applied stimulation and passive stimulation.

The present system extends the clinical efficacy of an FES exercise system, which is a paradigm for near isokinetic training which may be applied using a set of rules-based programs of exercise therapy that recommend certain programs for certain patients.

A further inventive development of the broad concept is to embodiments wherein there is the application of slow velocity isokinetic exercise (e.g. FES-induced cycling at 5-25 rev·min$^{-1}$) to build muscle strength and bulk, medium velocity isokinetic exercise (e.g. FES-induced cycling at 25-40 rev·min$^{-1}$) to promote leg muscle fatigue-resistance, and fast velocity isokinetic exercise (e.g. FES-induced cycling at 40-60 rev·min$^{-1}$) to promote enhanced cardiorespiratory fitness.

The present invention is directed to a system in which there is combined the use of a motor driven exercise machine with the user connected to an FES system via electrodes for activating selected muscle groups corresponding to those to be used on the exercise machine. In at least a preferred embodiment, a control system is deployed that receives signals via closed loop feedback, indicative of the user's performance during exercise, and the system is thus characterised as being a means for controlling the FES pulses to the user to maintain a substantially isokinetic exercise regime whereby average power output and/or average torque is the controlled outcome.

The controlling of the FES signals, advantageously, can be by manipulating current amplitude and timing and obtaining biofeedback to assist the user to perform exercise. Thus, one important aspect of the invention is to the FES system eliciting muscle contractions for a paretic or paraplegic user, but in the alternative, the system can be applied to those with impaired or normal voluntary muscle activation wherein the FES system simply assists such muscle contractions via sensory biofeedback.

At least in one form, the invention may be described as relating to a method of operation and a control system that establishes substantially isokinetic FES-induced exercising. This approach is believed to provide a significantly enhanced therapeutic effect compared with the exercise regimes that follow from use of the prior art.

The present inventors point out that their exercise regime directly contrasts with FES isometric exercise where there is substantially no movement of the limbs (but merely tensioning of the muscle groups in question). The present exercise regime also contrasts with FES concentric exercise where the velocity varies proportionately to the amount of force generated by the muscles. In the present regimen, the velocity of FES-induced limb movement remains constant, regardless of the force applied by the muscles. When applied to a bicycle type exerciser, usually the present invention would be implemented with the concept of maintaining a constant speed, for example 50 rev·min$^{-1}$ (revolutions per minute). When muscle power is generated in excess of that required to move the legs, the adaptive control loop operates to adjust both current to the motor to maintain constant velocity cycling and regulate FES pulses to the legs to maintain constant average power output. By simultaneously controlling both the motor and the stimulation pulses, the system can maintain both constant velocity and constant power/torque output regardless of whether the user can provide voluntary contractions in addition to those generated by electrical stimulation (i.e. FES).

A further inventive proposal is to control an exercise regime to permit muscles to perform a lengthy exercise session by arranging for relatively low speed initially, eg around 15 rev·min$^{-1}$, with subsequent exercise at higher speed, eg 40-50 rev·min$^{-1}$. A significant proposition is that this regime materially avoids premature fatiguing, thereby permitting more effective muscle training over an extended period.

Further particular inventive features associated with the present main inventive concept are operations whereby the FES pulses are controlled according to mathematical formulae that take into account the geometry of particular exercise machines and the set-up of a particular user on a machine. These formulae, as expressed in a computer model, calculate the most suitable pattern of firing FES pulses that are to be applied to each muscle of an individual user.

A second and independent inventive aspect associated with the present developments concerns the use of mathematical formula for the purposes described in the previous paragraph. However, broadly, this concept is considered applicable to various systems including FES systems that include those that are not motor driven.

Furthermore, the present invention can be applied in exercise regimes to recognise that different types of therapy can be achieved at different velocities of limb movements. For example, training at a relatively high speed will promote cardiorespiratory training, whereas slower speeds enhance the development of muscular strength. This speed-relative training can be applied to forms of therapy that utilise FES-induced muscle contractions, or therapies that employ voluntary muscle contractions by users.

In one aspect, the invention may be defined as consisting of an apparatus comprising a motor-driven exercise machine (for example, but not limited to a cycle exerciser), a functional electrical stimulation (FES) system for delivering stimulation to corresponding muscles of the user, and a control system to monitor the power applied to the electrical drive system of the motor as well as to control the timing, nature and duration of the FES pulses. The motor and FES control system act in response to measured performance, whereby the pedalling velocity is maintained at a user-specified substantially isokinetic rate while the muscles are simultaneously kept operating at a constant average power/torque output.

In one important manifestation of the present invention, there is provided an apparatus which includes a motor-driven exercise machine, an FES system for providing skin/muscle sensory biofeedback over corresponding muscles of a non-paralysed user and a feedback control system monitoring the power/torque applied to the electrical drive system of the motor to control the timing, nature and duration of the low current amplitude FES pulses in response to measured performance output by the user on the machine, whereby the speed of operation of the exercise machine can be pre-set to a desired constant velocity and substantially isokinetic FES exercise is thereby achieved.

Another important embodiment of the invention is for paralysed users; in this case, the invention may be defined as consisting in an apparatus including a motor-driven exercise machine such as a cycle exerciser, an FES system for the activation of corresponding muscles of a paralysed user, and a feedback control system monitoring the power/torque applied to the electrical drive system of the motor to control the timing, nature and duration of the FES pulses in response to measured performance output by the user on the machine, whereby the speed of operation of the exercise machine can be pre-set to a desired constant velocity and substantially isokinetic FES exercise is thereby achieved.

Ideally, the present invention would be implemented in a system providing Progressive Resistance Isokinetic Training (PRIT), typically on a cycle ergometer, although it appears that based on present commercially available cycles, pure isokinetic training is not achievable, but a close approximation is feasible. This application will be described, by way of example, in the following more detailed description. The present inventors believe that PRIT approach allows training individuals with neuromuscular disabilities such as spinal cord injury, hemiplegic stroke or traumatic brain injury in a new and valuable way using FES. FES induces leg muscle contractions, during constant-velocity leg cycling, under control of a computer with purpose built software to achieve substantially isokinetic exercise.

It is believed some particular disadvantages of prior art proposals, which at least in part are overcome by embodiments of the present invention, include the following:

(a) only an approximate-constant velocity of exercise, such as cycling, is achieved under the prior art feedback control that alter the FES current amplitude;
(b) generally, prior art proposals use fixed FES muscle firing patterns for all individuals and across all muscle groups;
(c) cycling velocity and muscle power could not both be independently monitored and controlled by prior art devices; and
(d) in prior art proposals, any attempt to quantify muscle fatigue has been imprecise due to the inability to calculate the peak power and torque during cycling.

It is believed that the above disadvantages and limitations have contributed to the lack of widespread acceptance of the prior art exercise devices as part of a rehabilitation process. Thus, a new and enhanced approach is required for there to be the perceived value and enhance results that are desirable in many patients.

In one aspect, the present invention may be defined as consisting in a software package for controlling and operating the system in the forms outlined in this specification. In preferred embodiments, newly developed algorithms control FES stimulation parameters in real-time such as waveform, pulse frequency, current amplitude on a pulse-by-pulse basis or muscle 'firing' angles.

In a preferred system, the user or therapist may select a desired velocity of cycling, and this will be maintained regardless of the state of the patient's muscle weakness or degree of fatigue during exercise. The control system thus facilitates patients effectively using the system at home without direct supervision of a therapist.

In the control system, the electrical stimulation to the user's muscles can be under active control to alter the precise timing of each stimulation pulse that can be achieved with, if required, variation of pulse width, stimulation frequency, waveform and current amplitude to elicit optimum stimulation of individual muscles. A preferred system also has means for recording information about training sessions (eg. FES parameters, peak and average power/torque outputs, etc) and users or therapists can customise the FES parameters and training sessions as desired. It is also preferred that the software can determine, and record for later analysis, specific timing for electrical stimulation pulses for each individual over the duration of a training session. In essence, the software is preferably arranged to operate in real time to facilitate maximising the training stimulus during an exercise session at a selected training velocity for a wide variety of users with physical disabilities.

In the embodiment of the current invention, calculation of exercise torque and power is achieved by monitoring the active exercise load derived from the power applied to the electrical motor of the machine. A significant feature of at least preferred embodiments of this invention is the ability to calculate real external loads of the muscles without including the passive load provided by the motor to move the legs.

In another aspect the present invention consists in a system to be adapted to be applied to a motor driven exercise machine, for example a cycling type machine.

Important embodiments of the invention are directed towards a system for achieving therapeutic exercise to paretic or paraplegic users but embodiments can be particularly beneficial for users having impaired or voluntary muscle control. For example, users having injury or disease may achieve rehabilitation or improvement in muscle performance by use of such embodiments.

Yet another aspect of the invention is directed to a software control system for the exercise regimes. Furthermore, the invention also manifests itself in methods of treatment or therapy using the novel approaches described therein.

EMBODIMENTS OF THE INVENTION

By way of example only, an embodiment of the invention will now be described with reference to Functional Electrical Stimulation (FES)-induced lower limb exercise using a cycle type machine in a system suitable for patients with neuromuscular disabilities such as (but not limited to) spinal cord injury. The embodiment described is a design for a FES Progressive Resistance Isokinetic Training (PRIT) cycle ergometer.

DETAILED DESCRIPTION OF THE DRAWINGS

Figure 1:
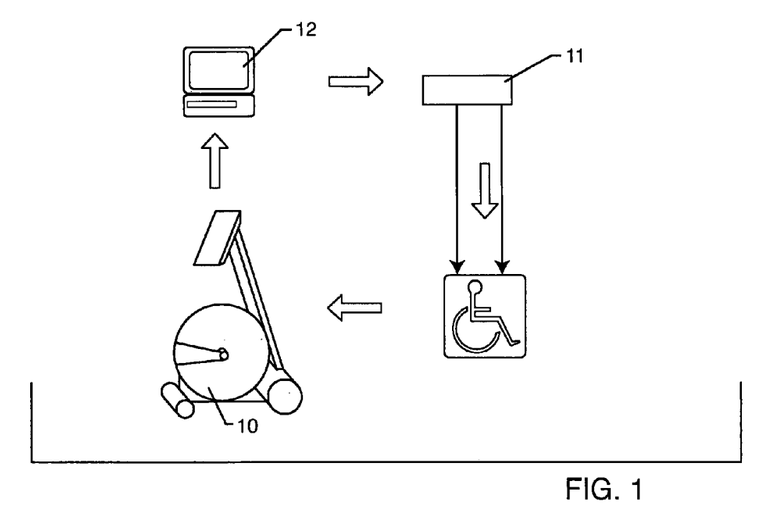
FIG. 1 is a schematic illustration of a system embodying the invention and including an exercise cycling machine on which a patient is to be seated.

The basic system is schematically illustrated in FIG. 1 with a patient arranged to be seated on a commercial driven cycle module (10), having electrical stimulation electrodes applied to the patient's muscles and stimulated by a FES device (11) under control of a computer (12) having novel software which monitors performance data derived from the cycle (10). A closed loop feedback system is provided with algorithms controlling the computer system to refine the FES parameters for the patient before and during PRIT cycle training.

The system may also be used with patients who do not require use of the FES module, although the computer system monitoring the cycle module (10) can be of value in controlling the average power or total work during a desired exercise regime and providing appropriate reports and monitoring. For such patients, PRIT may be equally applied based on visual and auditory biofeedback signals that inform the patients when to voluntarily activate their muscles.

In an alternative embodiment, the system may also be used with patients who require low current amplitude FES as a form of skin/muscle sensory biofeedback (known as BioFeedback Electrical Stimulation—"BioFES"), whereby the amplitude and timing of the FES pulses, with the computer system monitoring the cycle module (10), are of value in controlling the average power or total work during a desired exercise regime and providing appropriate reports and monitoring.

The commercial cycle (10) has its own speed control circuitry to maintain the preset pedalling cadence, for this purpose the cycle being driven by an electric motor. The cycle also transmits certain performance data (e.g. pedal position, pedal velocity and motor current) to the computer (12); such data is then used to control and calculate FES parameters that are to be used subsequently. The system calculates and monitors average power output or average torque that is used to control the exercise-training strategies.

The FES module (11) includes a micro controller that is controlled and reconfigured by alteration of the software running the computer system. In a preferred embodiment, alternative algorithms are available in the controlling software so that the therapist can vary the stimulation parameters to vary the relative contributions of various muscles to suit the particular patient. The principal design criteria and FES parameters of the FES module may be summarised as follows:

Six FES channels are provided and a system is driven from a low voltage battery power supply.

A current amplitude of up to 140 mA across a 1 kΩ load is pro ided

A pulse duration range of 50 µs to 500 µs is provided.

The pulse shape may be either square wave monophasic, square wave biphasic or a trapezoidal biphasic shape.

Unique patterns of stimulus pulses can be delivered under software control including (but not limited to) pulse doublets, pulse triplets, "catch-like" pulses and variable pulse duration "trains" of stimulation.

The stimulation frequency range of 5 Hz to 60 Hz is provided.

The timing of stimulation "firing angles" (defined as the time from FES pulse onset until cessation, for any particular muscle group) is under software or user control.

The computer system 12 can be any suitable PC with suitable operating software such as Microsoft Windows operating on an Intel Pentium processor. (Microsoft and Intel are trademarks.) The inventors have implemented an embodiment of the invention with a computer program developed using the LabView (Trade Mark) programming environment of National Instruments Incorporated. The principal functionality of the program includes the following aspects:

(i) monitoring and processing the information from the cycle ergometer module;

(ii) calculation of the optimum stimulation parameters in "real time";

(iii) determination of optimum muscle "firing angles" based on a computer model and mathematical equation to produce optimal FES cycling; and (iv) delivery of the stimulation parameter information to the FES module.

Figure 2:
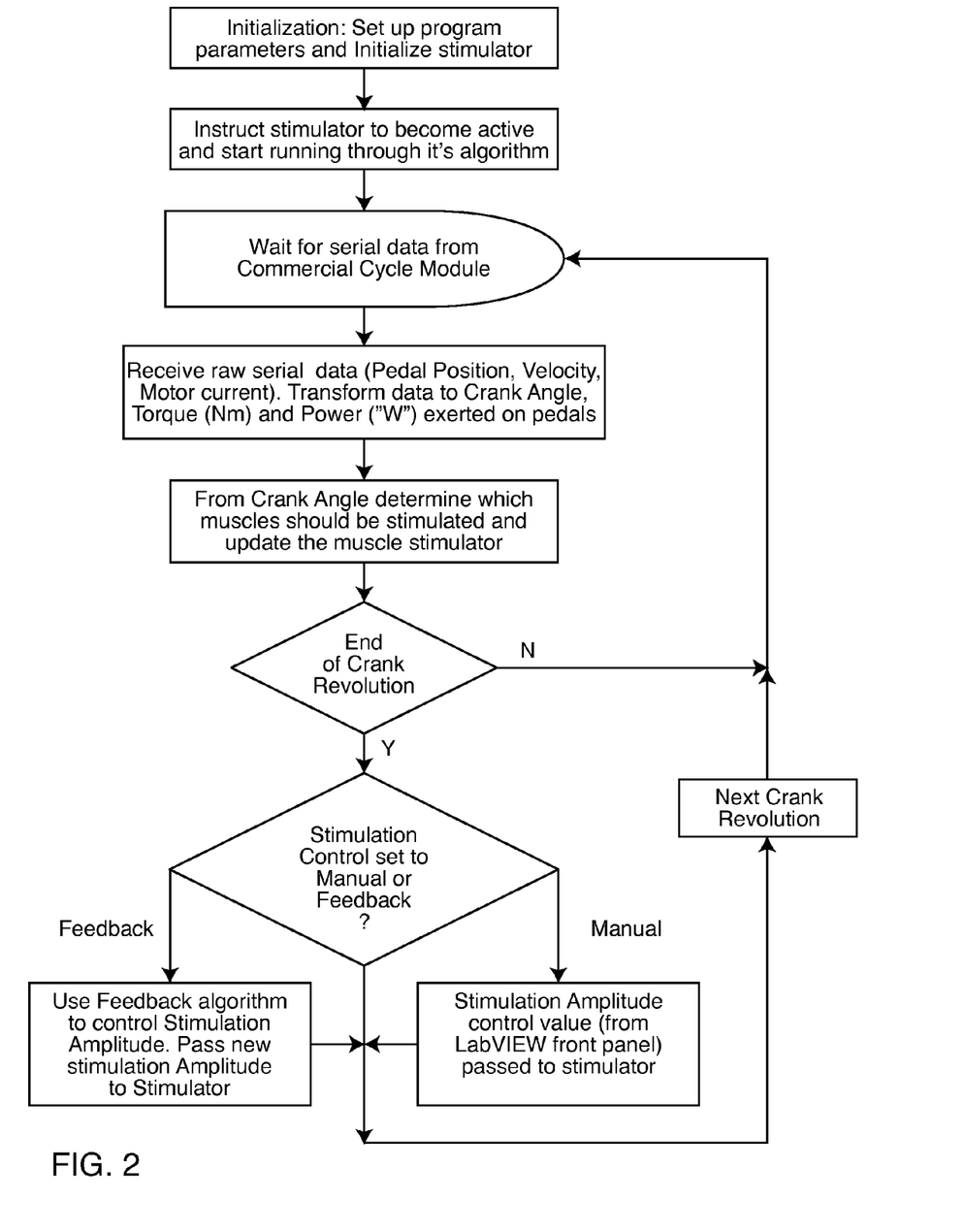
FIG. 2 is a flow chart illustrating the operation of system of FIG. 1 with isokinetic cycling.

Referring now to FIG. 2, there is a flow chart for FES isokinetic cycling which sets out the monitoring and processing of part (i) of the program. The cycle module transmits information on pedal position, pedal angle and motor current to the computer via a serial cable using RS-232 handshaking protocol at a rate of 38.4 KBaud. The instantaneous pedal position triggers stimulation delivery software. The motor current reflects the forces applied to the pedals and the software calculates instantaneous nett crank torque. Accurate calculation of peak power, average and peak torques during FES cycling are obtained.

Figure 3:
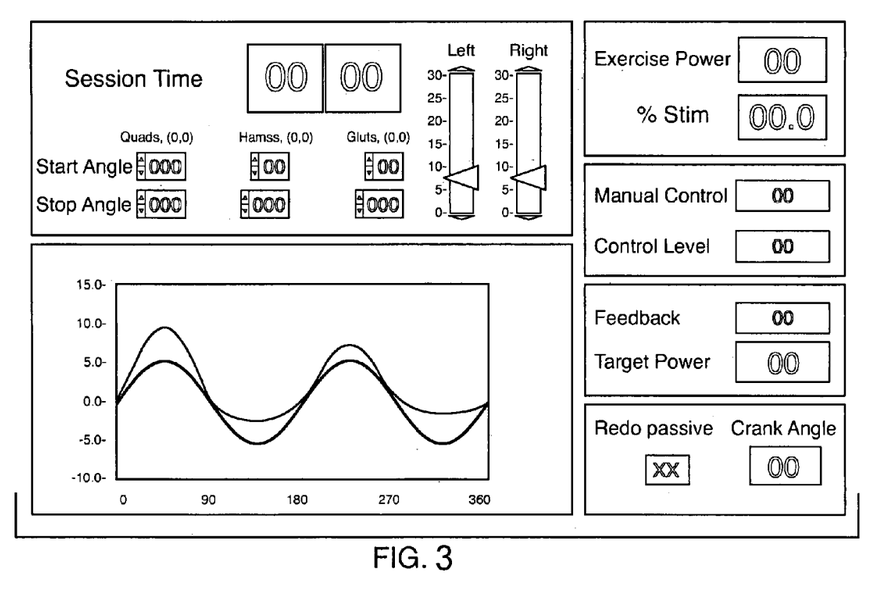
FIG. 3 is a typical display on a computer screen monitoring operation of the system of FIG. 1.

FIG. 3 is a typical display for a system and the lower left display shows a white line representing motorised passive cycling and a grey line representing active exercising and from this data the power and torque applied by the user is calculated in real time. Instantaneous pedal velocity is known from the monitoring software and is multiplied by crank torque to calculate the instantaneous power; the average power is subsequently calculated for the complete pedal revolution.

Average power output, which in FIG. 3 is shown as exercise power 7.9 watts in the upper right corner of the display, is an input variable to the second part of the software. Part (ii) of the software calculates command and control stimulation parameters. It is emphasised that this system contrasts with prior art systems that only modify stimulus amplitude in response to a changing (usually slowing) pedal cadence. The present system receives the average power output calculated from part (i) of the program and is compared to the desired or target value and the stimulation parameters are altered according to an adaptive equalisation controller algorithm. In the example shown in FIG. 3, a target power (found on the right hand side) has a value of 7.5 watts, but the actual exercise power determined at that time is 7.9 watts at 93.5% of peak stimulation amplitude. Accordingly, the stimulation applied to the user is reduced to change the exercise power towards the target value.

An alternative mode of controlling exercise with this embodiment is using, with the adaptive controller algorithm, a version programmed to minimise the rate of patient fatigue over time, to maximise the peak power per stroke, or to maintain an operator's selected average power output. The software also permits open-loop control of FES-induced cycling by not using the adaptive controller algorithm provided as a default feature. Thus, the algorithms can provide control through any combination of the FES parameters. The stimulation parameters are applied through part (iv) of the program described below.

Part (iii) of the program in this preferred embodiment includes a system for predicting suitable FES muscle firing angles based on distance measurements taken from the ergometer, the seat and having regard to the leg length of the individual user. The preferred program enables these firing angles to be determined for quadriceps, hamstrings and glutei muscles of paralysed persons and this is used in the initialisation part of the system operations depicted in FIG. 2.

Figure 4:
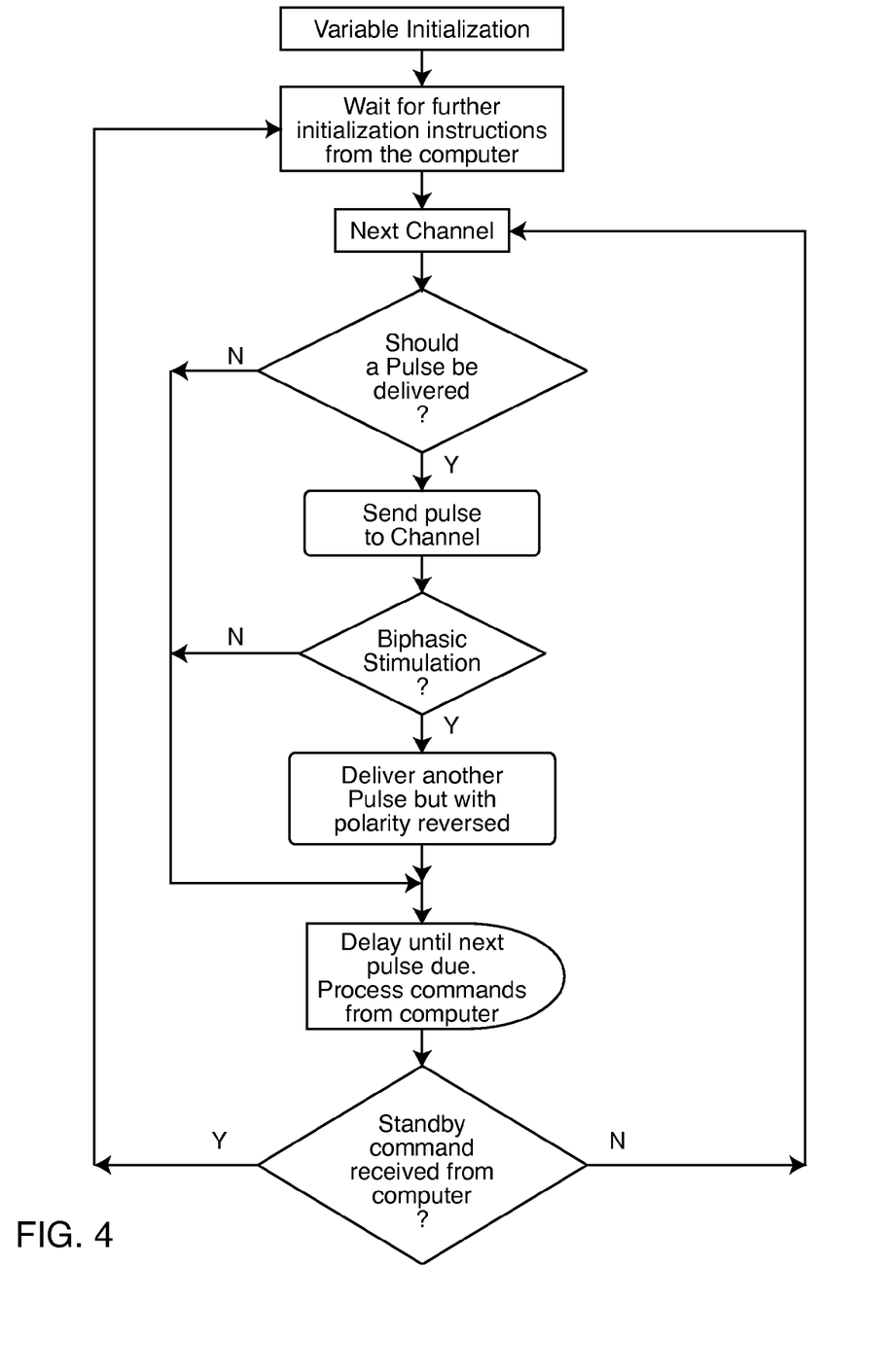
FIG. 4 is a schematic diagram of a software program for the FES module of FIG. 1.

Reference will now be made to FIG. 4 that illustrates the functionality of a control program for the FES module. This illustrates the manner in which appropriate stimulation is given.

Use of the present system extends to a FES PRIT exercise system, which is a paradigm for near isokinetic training using a set of rules-based programs of exercise therapy that recommend certain programs for certain patients. A key aspect is the application of slow velocity isokinetic exercise (e.g. FES-induced cycling at 10-15 rev·min$^{-1}$) to build muscle strength and bulk, medium velocity isokinetic exercise (e.g. FES-induced cycling at 25-40 rev·min$^{-1}$) to promote leg muscle fatigue-resistance, and fast velocity isokinetic exercise (e.g. FES-induced cycling at 40-60 rev·min$^{-1}$) to promote enhanced cardiorespiratory fitness.

Tests conducted by the inventors using the present system on patients with spinal paralysis have demonstrated that instantaneous power and average power is greatest at faster cycling speeds, whereas slow cycling demonstrates high torques, leading to augmented muscle strength.

Figure 5:
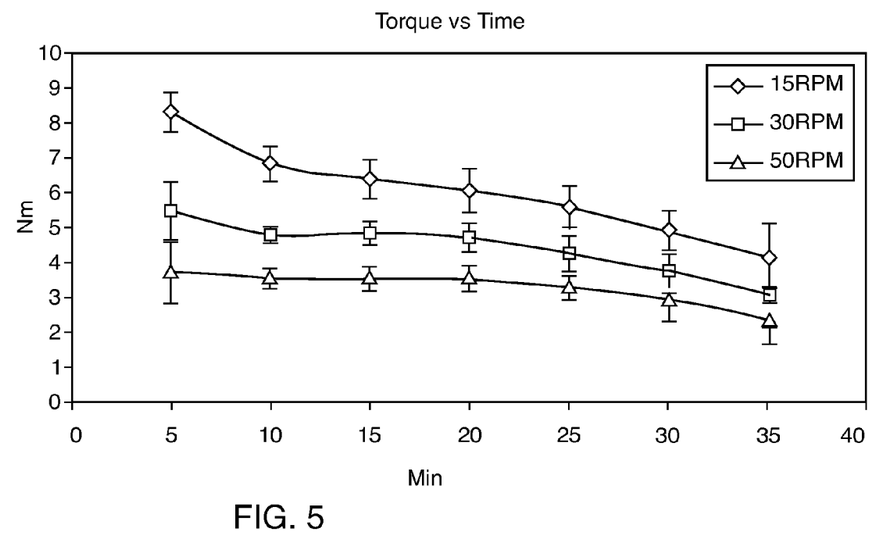
FIG. 5 illustrates average data for some five patients using the system of FIG. 1.
Figure 6:
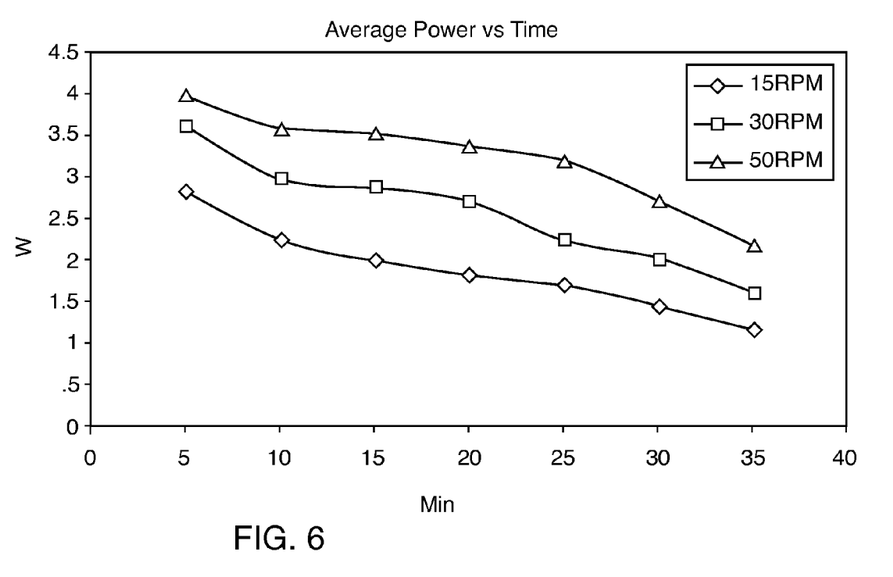
FIG. 6 illustrates data of power over a training or exercise time for average data from some 5 patients and corresponding to the exercise data of FIG. 5.

Referring to FIG. 5, average data for five patients is illustrated, showing measured torque values over time at respectively 15, 30 and 50 rev·min$^{-1}$ cycling velocity. These data demonstrate that peak torque (which is the muscle strength building component of exercise training) is highest at the slowest FES PRIT cycle velocity, and this advantage is maintained over a 35-minute training session. FIG. 6 demonstrates average power over time, and shows that average power (which is the cardiorespiratory fitness building component of exercise training) is highest at the fastest FES PRIT cycle velocity. This advantage is maintained over a 35-minute session.

The rules-based approach to training, in accordance with preferred therapy using the present invention, will assist the therapist to recommend how much time that the user should spend in each training session at any given cycling velocity from a wide range of possible velocities over a 0-60 rev·min$^{-1}$ range.

A further inventive aspect relates to the development and use of mathematical formulae expressed in a computer model to determine the optimum timing of FES pulses for cycling on any ergometer for any possible spinal cord-injured subject. This inventive aspect may also be applicable as a development having value in exercise systems wherein the machine does not have an electric motor drive (e.g. the commercial cycle (10)), but is solely driven by the user via concentric exercise.

In overview, the further inventive aspect is concerned with analyzing the geometric relationship between a particular spinal cord-injured patient's lower limbs, the geometry of the machine and the position at which the user is located, and developing appropriate control-to-patterns for the timing and nature of FES pulses. This contrasts with prior art systems where there has simply been preset timing of FES pulses over a muscle's "firing angle" (i.e. the time from FES pulse onset until cessation for any particular muscle group) relative to absolute pedal crank positions.

The mathematical modelling takes measurements from (i) the length of the cycle crank, (ii) length of the subject's thigh from hip to knee, (iii) length of the foreleg measured from the pedal to the knee, (iv) horizontal and vertical distances from the cycle's crank axle to the subject's hip when seated, and (v) speed of FES-induced cycling. From these measurements, a unified mathematical formula expressed as a computer model determines the range of cycle crank angles wherein it is advantageous to have each muscle generating force.

This geometric relationship is modified by taking into account the time taken for paralysed muscles to contract and relax in response to onset and cessation of FES-induced muscle contractions. Extensive experimental evidence of the timing for onset and cessation of FES-induced muscle contractions have been used to determine the appropriate FES pulse durations and "firing angles" for subjects with spinal cord injuries. The combination of geometric formulae and timing of force development are then used to determine the most suitable crank angles for use within the adaptive controller algorithm.

The geometric relationship can be defined using the following variables:

Variables Measured from the Subject and the Ergometer
  seatang The angle the seat is reclined from the vertical,
  dhoriz The horizontal distance between a subject's hip and the cycle ergometer's axle,
  dvert The vertical distance between a subject's hip and the cycle ergometer's axle,
  lt The subjects thigh length, from hip to knee,
  ls The subject's shank length, measured from the knee to the axle of the pedal, including any thickness of the pedal and footwear,
  lc The ergometer crank length.

Variables Derived from Previously Published Research
  dhk Moment arm of the hamstring muscles about the knee,
  dhh Moment arm of the hamstring muscles about the hip,
  dqk Moment arm of the quadriceps muscles about the knee,
  dgh Moment arm of the gluteal muscles about the hip.

From the measured variables, the subject's knee and hip angles at any particular crank angle (qc) may be calculated from the following formulae:

$$\text{Shank angle} = Pi - \text{ArcCos}[(dhoriz^2 + dvert^2 + lc^2 + ls^2 - lt^2 + 2*dhoriz* \\ lc*\text{Cos}[qc] + 2*dvert*lc* \\ \text{Sin}[qc])/(2*ls*\text{Sqrt}[dhoriz^2 + dvert^2 + lc^2 + 2* \\ dhoriz*lc*\text{Cos}[qc] + 2*dvert*lc*\text{Sin}[qc]])] - \\ \text{ArcTan}[(dvert + lc*\text{Sin}[qc])/(dhoriz + lc*\text{Cos}[qc])]$$

$$\text{Thigh angle} = 2*Pi - \text{ArcCos}[-((dhoriz^2 + dvert^2 + lc^2 - \\ ls^2 - lt^2 + 2*dhoriz*lc*\text{Cos}[qc] + \\ 2*dvert*lc*\text{Sin}[qc]/(2*ls*lt))] - \\ \text{ArcCos}[(dhoriz^2 + dvert^2 + lc^2 + ls^2 - lt^2 + \\ 2*dhoriz*lc*\text{Cos}[qc] + 2*dvert*lc*\text{Sin}[qc])/ \\ (2*ls*\text{Sqrt}[dhoriz^2 + dvert^2 + lc^2 + 2*dhoriz* \\ lc*\text{Cos}[qc] + 2*dvert*lc*\text{Sin}[qc]])] - \\ \text{ArcTan}[(dvert + lc*\text{Sin}[qc])/(dhoriz + lc*\text{Cos}[qc])]$$

These geometric relationships, together with estimations of the respective moment arm of each muscle about the hip and knee joints, enable the determination of those crank angles where muscle force will generate assist propulsion of the ergometer. For the quadriceps, hamstring and gluteal muscles, the muscles should be generating force at crank angles where the following formulae produce positive values:

Quadriceps $$(-((lc*Csc[qs-qt]*dqk*(ls*Sin\ [qc+qs]+lt*Sin\ [qc+qt]))/(ls*lt)))$$

Hamstrings $$(lc*Csc[qs-qt]*(-(ls*dhh*Sin\ [qc+qs])+ls*dhk*Sin\ [qc+qs]+lt*dhk*Sin\ [qc+qt]))/(ls*lt)$$

Gluteals $$-(lc*Csc[qs-qt]*dgh*Sin\ [qc+qs])/lt$$

Extensive measurements have been taken by the inventors with respect to the time taken for paralysed muscles to contract and relax in response to electrical stimulation. For each muscle a particular time is required for the muscle to generate force after stimulation commences, and a different time for the muscle to relax. This experimental data, with advantage, is used to optimise treatment regimes.

FES firing angles for each muscle may-be determined for specific individual subjects and ergometer positions by solving the above formulae to determine crank angles where muscle force is desired, then advancing this crank angle by the appropriate force generation time multiplied by the velocity of cycling to give the appropriate FES onset angle. Similarly, FES cessation angles may be determined by using the above formulae then advancing the cessation angle by the cycling velocity multiplied by the appropriate relaxation time constant.

In this way, FES firing angles may be determined for use within the adaptive controller algorithm. Once the maximum range of suitable firing angles is calculated, the actual range used while cycling would likely be reduced in order to increase the duration of rest between successive muscle contractions. Use of these formulae would enable any future knowledge of the ideal work to rest ratio during FES induced contractions to be incorporated within the adaptive controller algorithm.

Use of these formulae is not limited to the present system using an isokinetic cycle ergometer and control systems based on measurement of instantaneous crank position. These formulae may be applied to any ergometer system where there is not substantial movement at the ankle joint (which would produce a variable shank length within the present definition). Furthermore, the geometric formulae linking thigh and shank angle to crank position enable the development of future control systems based on direct measurement of segment positions, rather than being reliant upon feedback of crank position from the ergometer.

The invention claimed is:

1. A system including:
   (a) an exercise machine having displaceable means for moving with a body part of a user;
   (b) a motor arranged to drive the displaceable means at a selected but normally substantially constant speed and providing a resistance for resisting displacement load from the user's body part applied to the displacement means;
   (c) a functional electrical stimulation (FES) system for selected muscle groups of the user corresponding to the body part to be exercised on the exercise machine;
   (d) a feedback control system that receives signals indicative of the user's performance during exercise; and
   (e) means for controlling the FES system, by controlling the electrical stimulation to the user's muscles to control the exercise regime; and
   (f) means to measure and provide output data for recording the muscle performance of the user; and
   (g) means for controlling an exercise regime for the user with means responsive to the data relating to the user's muscle performance to select different speeds for the motor and different corresponding timings for stimulation through the FES to vary the work load.

2. A system as claimed in claim 1, wherein the FES system has means for eliciting muscle contractions via controlling the amplitude of electrical stimulation for a paretic or paraplegic user.

3. A system as claimed in claim 1 and wherein the FES system has means adapted to assist muscle contraction to select muscles of a user having impaired or voluntary muscle control.

4. A system as claimed in claim 1 wherein during an exercise session the system initially establishes a relatively low speed of exercise and subsequently adopts a higher speed or speeds, whereby early fatiguing of the user's muscles is obviated and longer exercise training sessions are provided.

5. A system as claimed in claim 4 and wherein an initial exercise speed for a user not having voluntary muscle control or with impaired muscle control is at about 5-25 rev·min$^{-1}$ and subsequently during the exercise session the speed is increased to of the order of 40-60 rev·min$^{-1}$.

6. A system as defined in claim 1 wherein the system includes an adaptive control loop to adjust the motor to maintain constant velocity motion in the machine and/or to regulate FES pulses to the user's muscles to maintain a user-selected average power and/or average torque output during exercise irrespective of any voluntary muscle contractions of the user additional to those generated by the electrical stimulation.

7. A system as claimed in claim 1 when the controlling means has means allowing the user to utilise substantially isokinetic exercise at different velocities of limb movement to elicit different patient outcomes suitable for promoting muscular strength, muscle fatigue-resistance or cardiorespiratory fitness via FES muscle recruitment or voluntary muscle activation.

8. A system as claimed in claim 7, and comprising means to control an exercise regime and having means to maintain a relatively slow speed for an initial exercise segment followed by a relatively high speed segment.

9. A system including:
   (a) an exercise machine having displaceable means for moving with a body part of a user;
   (b) a motor arranged to drive the displaceable means at a selected but normally substantially constant speed and providing a resistance for resisting displacement load from the user's body part applied to the displacement means;
   (c) a functional electrical stimulation (FES) system for selected muscle groups of the user corresponding to the body part to be exercised on the exercise machine;
   (d) a feedback control system that receives signals indicative of the user's performance during exercise;
   (e) means for controlling the FES system, by controlling the electrical stimulation to the user's muscles to control the exercise regime; and
   (f) means for controlling FES pulses according to mathematical formulae that take into account the geometry of particular exercise machines and the set-up of a particular user on a machine.

10. A system including:
an exercise machine having displaceable means for moving with a body part of a user;
a motor arranged to drive the displaceable means at a selected but normally substantially constant speed and providing a resistance for resisting displacement load from the user's body part applied to the displacement means;
a functional electrical stimulation (FES) system for selected muscle groups of the user corresponding to the body part to be exercised on the exercise machine;
a feedback control system that receives signals indicative of the user's performance during exercise;
means for controlling the FES system, by controlling the electrical stimulation to the user's muscles to control the exercise regime; and
means for determining, for a particular user, a desired set of timing data for the FES system, and means for applying the data to control FES pulses to selected muscles of the user when using the exercise machine; wherein the exercise machine provides cycling exercise and the means for determining data uses formulae from a mathematical model which determines firing angles for the exercise machine based on all or some of the following factors:
(i) the length of the cycle crank,
(ii) length of the subject's thigh from hip to knee,
(iii) length of the foreleg measured from the pedal to the knee,
(iv) horizontal and vertical distances from the cycle's crank axle to the subject's hip when seated, and
(v) speed of FES-induced cycling.

11. An apparatus including a motor-driven exercise machine, an FES system for providing skin/muscle sensory biofeedback over corresponding muscles of a non-paralysed user and a feedback control system monitoring the power/torque applied to the electrical drive system of the motor to control the timing, nature and duration of relatively low current amplitude FES pulses in response to measured performance output by the user on the machine, the speed of operation of the exercise machine being controllable to a desired constant speed and substantially isokinetic FES exercise is thereby achieved.

12. An apparatus as claimed in claim 11 wherein the apparatus is a cycling apparatus wherein a drive system to the motor controls the motor to constant speed and the amplitude of the FES pulses are controlled in accordance with the response from the biofeedback, the FES being adapted to stimulate muscles comprising the hamstrings, glutei and quadriceps.

13. An apparatus including a motor-driven exercise machine, an FES system for the activation of corresponding muscles of a paralysed user, and a feedback control system monitoring the power/torque applied to the electrical drive system of the motor to control the timing, nature and duration of the FES pulses in response to measured performance output by the user on the machine, the speed of operation being controlled to a desired constant velocity and substantially isokinetic FES exercise is thereby achieved.

14. An apparatus as claimed in claim 13 wherein the apparatus is a cycling apparatus wherein a drive system to the motor controls the motor to constant speed and the amplitude of the FES pulses are controlled in accordance with the response from the biofeedback, the FES being adapted to stimulate muscles comprising the hamstrings, glutei and quadriceps.

15. A control system for application to an exercise machine for exercising a body part of the user and wherein the exercise machine has displaceable means for moving with the body part of the user and a motor arranged to drive the displaceable means at a selected but normally constant speed and providing a resistance for resisting displacement load from the user's body part applied to the displacement means, and a functional electrical stimulation (FES) system for selected muscle groups of the user corresponding to the body part to be exercised on the exercise machine, and the control system having
(a) means for controlling the motor to operate normally at substantially constant speed and provide a resisting displacement load from the user;
(b) a feedback control system that receives signals indicative of the user's performance during exercise; and
(c) means for controlling the FES system by controlling the electrical stimulation to the user's muscles to control the exercise regime.

16. A control system as claimed in claim 15 and wherein the feedback control system is a close loop feedback system adapted to modify the amplitude of FES signals in real time responsive to performance of the user's muscles, the FES system being adapted to be applied to a circular cycling motion through stimulation of quadriceps, hamstrings and glutei.

17. A control system as claimed in claim 16 and including means responsive to the feedback control system to theoretically alter the speed of the motor driven exercise machine during an exercise regime.

18. A control system for apparatus as claimed in claim 6 and having a computer control means using code for implementing mathematical formulae expressed in a computer model that calculate selected patterns for selected muscles, and has means for adapting the nature of FES pulses to particular muscles taking into account the geometry of particular exercise machines and the set up of a particular user on a particular machine.

19. A control system as claimed in claim 18 and having means for utilising open loop control of the FES pulses to cause electrodes attached to the user to provide electrical stimulation to muscles corresponding to the therapy desired to maintain a substantially isokinetic exercise regime.

20. A control system as claimed in claim 18 and having means for processing closed loop feedback signals by monitoring the motor of the exercise machine, and adapted to provide control signals to cause the FES system to elicit electrical stimulation to muscles corresponding to the therapy desired to maintain a substantially isokinetic exercise regime.

21. A control system as claimed in claim 18, wherein the FES system is arranged to stimulate muscles of the user based on a cycling exercise regime using an algorithm based on the following formulae defining the user's knee and hip angles at any particular crank angle (qc)

Shank angle =

$$Pi - \text{ArcCos}[(dhoriz^2 + dvert^2 + lc^2 + ls^2 - lt^2 + 2*dhoriz*$$
$$lc*\text{Cos}[qc] + 2*dvert*lc*$$
$$\text{Sin}[qc]/(2*ls*\text{Sqrt}[dhoriz^2 + dvert^2 + lc^2 + 2*$$

-continued $$dhoriz*lc*\text{Cos}[qc]+2*dvert*lc*\text{Sin}[qc]])-$$
$$\text{ArcTan}[(dvert+lc*\text{Sin}[qc])/(dhoriz+lc*\text{Cos}[qc])]$$

Thigh angle = $2*Pi - \text{ArcCos}[-((dhoriz^2+dvert^2+lc^2-$
$ls^2-lt^2+2*dhoriz*lc*\text{Cos}[qc]+$
$2*dvert*lc*\text{Sin}[qc]/(2*ls*lt))]-$
$\text{ArcCos}[(dhoriz^2+dvert^2+lc^2+ls^2-lt^2+$
$2*dhoriz*lc*\text{Cos}[qc]+2*dvert*lc*\text{Sin}[qc])/$
$(2*ls*\text{Sqrt}[dhoriz^2+dvert^2+lc^2+2*dhoriz*$
$lc*\text{Cos}[qc]+2*dvert*lc*\text{Sin}[qc]])]-$
$\text{ArcTan}[(dvert+lc*\text{Sin}[qc])/(dhoriz+lc*\text{Cos}[qc])]$ where
- seatang is the angle the seat is reclined from the vertical,
- dhoriz is the horizontal distance between a subject's hip and the cycle ergometer's axle,
- dvert is the vertical distance between a subject's hip and the cycle ergometer's axle,
- lt is the subject's thigh length, from hip to knee,
- ls is the subject's shank length, measured from the knee to the axle of the pedal, including any thickness of the pedal and footwear,
- lc is the ergometer crank length;
- dhk is the moment arm of the hamstring muscles about the knee,
- dhh is the moment arm of the hamstring muscles about the hip,
- dqk is the moment arm of the quadriceps muscles about the knee,
- dgh is the moment arm of the gluteal muscles about the hip;

and stimulating muscles to generate force when the following have positive values Quadriceps $(-((lc*\text{Csc}[qs-qt]*dqk*(ls*\text{Sin }[qc+qs]+lt*\text{Sin }[qc+qt]))/(ls*lt)))$ Hamstrings $(lc*\text{Csc}[qs-qt]*(-(ls*dhh*\text{Sin }[qc+qs])+ls*dhk*\text{Sin }[qc+qs]+lt*dhk*\text{Sin }[qc+qt]))/(ls*lt)$ Gluteals $-(lc*\text{Csc}[qs-qt]*dgh*\text{Sin }[qc+qs])/lt$.

22. A method of treatment of muscles in a user comprising using a system as claimed in any one of claim 1-10 or 15-21 or apparatus as claimed in any one of claims 11-17.

23. A method of exercising a body part of a user, the method including
 (a) using a displacement means of an exercise machine to cause the body part to move with the displacement means,
 (b) externally driving said displacement means by driving means,
 (c) controlling the external driving means to maintain substantially constant speed movement of the displacement means, at least during a portion of the movement,
 (d) applying electrical stimulation to the muscles associated with the body part for stimulating the muscles to move the body part for applying some drive force to the displacement means while the displacement means continues to be displaced under the influence of the external driving means,
 (e) monitoring the motion of the body part and/or displacement means, monitoring the driving means and determining the user's performance,
 (f) adjusting stimulation parameters for the applied electrical stimulation to achieve a desired user performance for the body part, and
 (g) delivering electrical stimulation to the muscles during the exercise in accordance with the determined stimulation parameters.

24. A method of exercising as claimed in claim 23, and further controlling the exercise to be substantially isokinetic during at least a principal portion on each movement.

* * * * *